(12) United States Patent
Shen

(10) Patent No.: US 11,611,838 B2
(45) Date of Patent: Mar. 21, 2023

(54) SYSTEM AND METHOD FOR INDIVIDUALIZED HEARING AIR PRESCRIPTION

(71) Applicant: The Trustees of Indiana University, Bloomington, IN (US)

(72) Inventor: Yi Shen, Bloomington, IN (US)

(73) Assignee: The Trustees of Indiana University, Bloomington, IN (US)

(*) Notice: Subject to any disclaimer, the term of this patent is extended or adjusted under 35 U.S.C. 154(b) by 124 days.

(21) Appl. No.: 17/309,945

(22) PCT Filed: Jan. 9, 2020

(86) PCT No.: PCT/US2020/012899
§ 371 (c)(1),
(2) Date: Jul. 2, 2021

(87) PCT Pub. No.: WO2020/146608
PCT Pub. Date: Jul. 16, 2020

(65) Prior Publication Data
US 2022/0078564 A1    Mar. 10, 2022

Related U.S. Application Data

(60) Provisional application No. 62/790,286, filed on Jan. 9, 2019.

(51) Int. Cl.
*H04R 25/00* (2006.01)
*A61B 5/12* (2006.01)

(52) U.S. Cl.
CPC ............. *H04R 25/70* (2013.01); *A61B 5/123* (2013.01); *H04R 25/43* (2013.01); *H04R 25/505* (2013.01);

(Continued)

(58) Field of Classification Search
CPC ....... H04R 25/00; H04R 25/30; H04R 25/305
See application file for complete search history.

(56) References Cited

U.S. PATENT DOCUMENTS

2006/0210090 A1    9/2006  Shennib
2014/0270190 A1    9/2014  Flynn et al.
(Continued)

*Primary Examiner* — Suhan Ni
(74) *Attorney, Agent, or Firm* — Woodard, Emhardt, Henry, Reeves & Wagner, LLP

(57) ABSTRACT

Disclosed is a system and method for individualized hearing aid prescription which consists of a test procedure that enables the fitting of an individualized estimation of the SII model to individual listeners efficiently and an optimization process which translates the resulting individualized model to the prescribed gains across frequencies for programming into the user's hearing aids. The test involves the recognition of one or more words presented in background noise, which better approximates the daily listening experiences of hearing-aid users compared to the pure-tone detection in a silent environment task which is commonly utilized during conventional audiometric testing. In the estimated SII model, five parameters describe in a custom fashion the relative weights of speech information across the five frequency bands for a given listener. The results from the speech test is used to determine the desirable amount of gain for each frequency region to optimize the user's aided speech intelligibility. The resulting gains for the individual may then be programmatically applied to the individual's prescribed hearing aid device(s).

16 Claims, 3 Drawing Sheets

(52) U.S. Cl.
CPC ...... *H04R 2225/43* (2013.01); *H04R 2430/01* (2013.01)

(56) References Cited

U.S. PATENT DOCUMENTS

| | | |
|---|---|---|
| 2015/0025413 A1 | 1/2015 | Shennib |
| 2015/0078561 A1* | 3/2015 | Brungart .............. H04R 29/008 381/60 |
| 2015/0021571 A1 | 7/2015 | Francart et al. |
| 2015/0208956 A1 | 7/2015 | Schmitt |
| 2015/0289062 A1* | 10/2015 | Ungstrup ............. H04R 25/554 381/314 |
| 2016/0235328 A1 | 8/2016 | Elberling et al. |
| 2017/0245063 A1* | 8/2017 | Jensen .................... H04R 3/04 |
| 2020/0068324 A1* | 2/2020 | Perscheid ............. H04R 25/70 |

* cited by examiner

SYSTEM AND METHOD FOR INDIVIDUALIZED HEARING AIR PRESCRIPTION

CROSS REFERENCE TO RELATED APPLICATIONS

The present application claims the benefit of U.S. Provisional Patent Application Ser. No. 62/790,286 filed Jan. 9, 2019 entitled "SYSTEM AND METHOD FOR INDIVIDUALIZED HEARING AID PRESCRIPTION" which is hereby incorporated by reference in its entirety to the extent not inconsistent.

NOTICE OF FEDERAL FUNDING

This invention was made with government support under DC013406 awarded by the National Institutes of Health. The government has certain rights in the invention.

FIELD OF THE INVENTION

The present disclosure relates to the prescription of hearing aids and, more specifically, to systems and methods for prescribing hearing-aids based upon user specific hearing levels which are analyzed across a range of audible frequencies, including during the presence of background noise and to effecting the programming of hearing-aids utilizing the determined prescription.

BACKGROUND OF THE INVENTION

It is estimated that thirteen percent of the U.S. adult population has some level of hearing deficiency in both ears. This hearing deficiency can range from profound deafness to hearing loss which prevents the individual from easily hearing sounds. Any level of hearing loss may limit or prevent an individual's ability to understand speech. While there are many physiological reasons for hearing deficiencies, the most common method of correction is the use of an auditory prosthesis (e.g. a hearing aid).

Hearing aids are well-known in the art and include a microphone for converting environmental sounds into an electrical signal, an amplifier for amplifying the electrical signal and a speaker for converting the amplified electrical signal back into a sound for delivery to the wearer's ear. Hearing aids can be configured for wear by the user in a case that is carried by an ear piece behind the ear (typically called a BTE device), in a case that is physically placed at least partially in the external ear canal (typically called an ITE device) or in a case which can be physically placed within the external ear canal (typically called an ITC device). While these types of hearing aids differ from each other in physical size and intended placement, they all include similar components which serve to amplify the auditory environment to enhance the hearing of the user.

Hearing aids do not amplify all sound, rather they selectively amplify and filter sound so that the individual can hear and ideally understand more of the sounds that the individual desires. As such, much like eyeglasses, each hearing aid must be custom fit to its wearer and their specific hearing ability and environment. In most cases, an individual's hearing loss is not uniform over the entire frequency spectrum of hearing. An individual's hearing loss may be greater at higher frequencies than at lower frequencies, typical of noise induced high frequency hearing loss. Also, the degree of loss at the higher frequencies varies with individuals and the frequency at which the loss begins also varies. The measurement by which an individual's hearing loss, or, put conversely, the individual's hearing ability, is called an audiogram. Traditionally, a hearing health professional, such as an audiologist, measures the individual's perceptive ability for differing sound frequencies and differing sound amplitudes using test pure tones presented in a quiet environment. The results are plotted in an amplitude/frequency diagram which graphically represents the individual's hearing ability, and, hence, the individual's hearing loss as compared with normal hearing individuals.

Since different individual have differing hearing losses (and, hence, hearing abilities), hearing aids typically are made to be adjustable to compensate for the hearing deficiency of the individual user. Typically, the adjustment involves an adjustable filter, used in conjunction with the amplifier, for modifying the amplifying characteristics of the hearing aids. Some typical hearing aids are adjustable by physically turning screws or thumb-wheels to adjust potentiometers or capacitors to modify the auditory characteristics, e.g., filtering characteristics, of the hearing aid.

More recently, programmable hearing aids have become well known. A programmable hearing aid typically has a digital control section which stores an auditory parameter, or set of auditory parameters, which control a particular aspect, or aspects, of the signal processing characteristics of the hearing aid and has a signal processing section, which may be analog or digital, which operates in response to the control section to perform the actual signal processing, or amplification. In some hearing aids, the control section may have the ability to store a plurality of sets of auditory parameters which the individual or other device may select for use.

Unfortunately, the significant majority of Americans who have hearing deficiencies and would benefit from the use of hearing aids do not utilize them for one reason or another. While some cannot afford the costs of hearing aids, which are not always covered by insurance, many other Americans do not utilize hearing aids as they are or have been dissatisfied with hearing aid performance, which is often attributable to their particular hearing aid prescription and its inability to accurately provide the level of hearing assistance that they need.

One of the predominant goals of future hearing health care is to provide individualized services to meet the individual needs of hearing-impaired patients. However, most hearing aids are still prescribed using a one-size-fits-all approach. That is, the same amount of amplification would be prescribed during the initial hearing-aid fitting to different patients as long as these patients have matching audiometric thresholds (i.e. based on the ability in detecting pure tones in quiet). While traditional hearing-aid fitting may tailor the device to individual user's audiometric thresholds, hearing-impaired listeners with similar thresholds could still exhibit large individual differences in speech understanding. Therefore, just measuring patients' abilities in hearing pure tones appears to be insufficient and more comprehensive profiling of individual hearing-aid users may be beneficial. The current invention aims to address the issues in the current hearing-aid prescription process and provide a procedure to optimize the amplification prescription for each individual hearing-aid user.

DESCRIPTION OF THE ILLUSTRATED EMBODIMENTS

Figure 1:
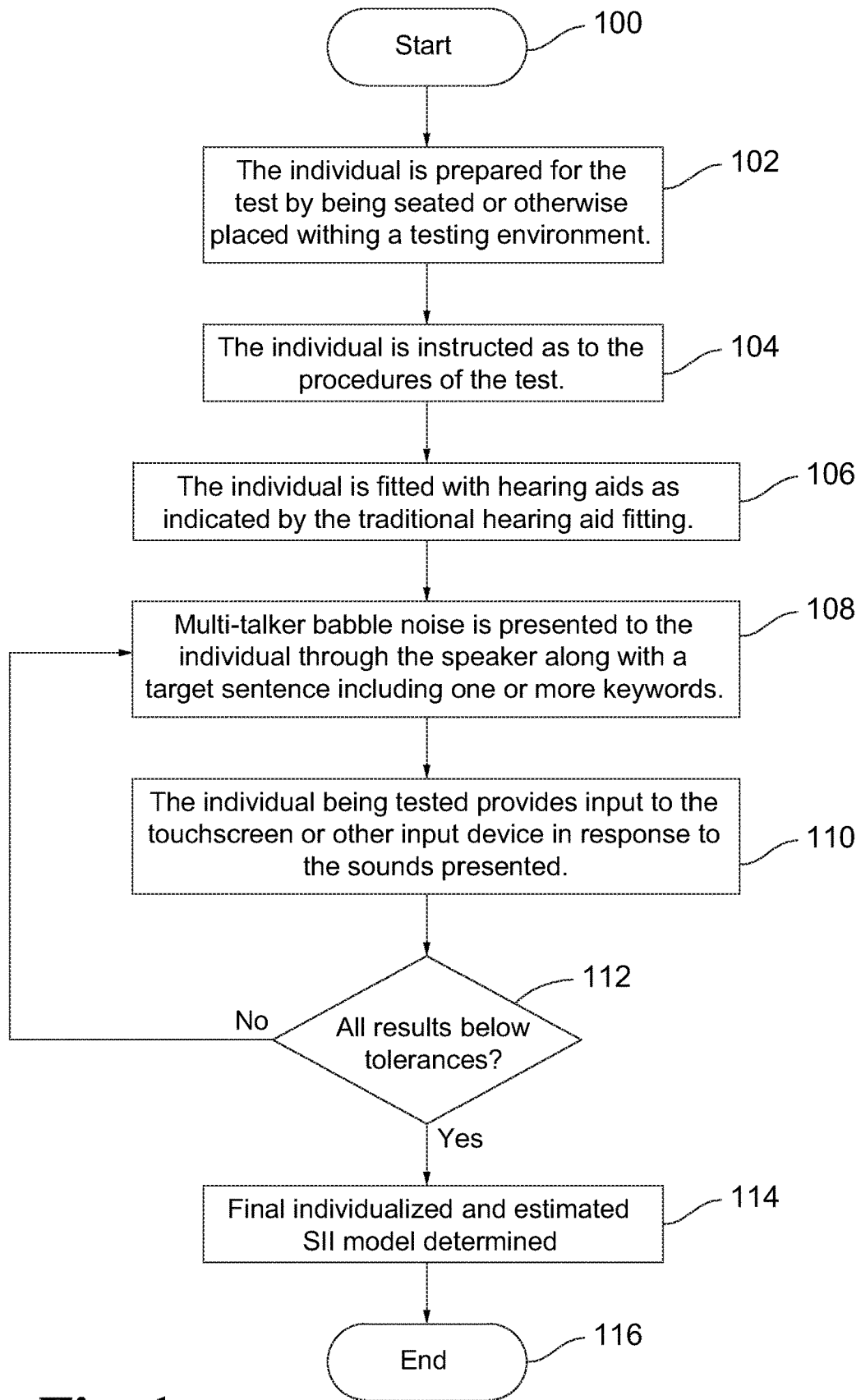
FIG. 1 is a flowchart illustrating an exemplary process for testing and the hearing of an individual being fit for hearing aids and refining the results.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

Existing hearing-aid prescription formulas are based on a well-established model of speech intelligibility, namely the Speech Intelligibility Index ("SII"). The SII is a quantification of the proportion of speech information that is both audible and usable for a given listener. Basically, an SII of 0 implies that none of the speech information, in a given setting, is available (audible and/or usable) to improve speech understanding. An SII of 1.0 implies that all the speech information in a given setting is both audible and usable for a listener. Generally, there is a monotonic relationship between the SII and speech understanding. That is, as the SII increases, speech understanding generally increases. The method for calculating the SII is described in the ANSI S3.5 (1997) standard titled "American National Standard Methods for Calculation of the Speech Intelligibility Index," which is hereby incorporated by reference.

The SII model is commonly used to predict the average speech recognition performance expected from a user based on their personal audiometric thresholds. That is, the predictions from the SII model would only differ for two listeners when these listeners show differences in audiometric thresholds. However, it has been well know that listeners with similar audiograms could exhibit large differences in speech recognition. This result is due to the fact that the SII model assumes that all listeners utilize speech information across various frequency regions equally and that the only factor that may contribute to individual differences in speech intelligibility is the hearing thresholds at those frequencies. Research conducted by the applicant has shown that this assumption is invalid in many situations and fitting the SII model to individual listeners improves the prediction of the individual listeners' performance in recognizing speech, particularly speed which is presented in background noise which is often the case in real world settings. Accordingly, what is needed is a predictive model of speech recognition that captures the consequences of these supra-threshold deficits for individual listeners.

In one embodiment, the disclosed system and method for individualized hearing aid prescription consists of a test procedure that enables the fitting of an individualized estimation of the SII model to individual listeners efficiently and an optimization process which translates the resulting individualized model to the prescribed gains across frequencies for programming into the user's hearing aids. In the form described herein, the test involves the recognition of one or more words presented in background noise, which better approximates the daily listening experiences of hearing-aid users compared to the pure-tone detection in a silent environment task which is commonly utilized during conventional audiometric testing. In the estimated SII model, five parameters describe the relative weights of speech information across the five frequency bands for a given listener. These parameters form a Band Importance Function (BIF), which represents which spectral regions that the listener relies on for speech recognition in background noise. A Bayesian adaptive procedure, referred to herein as the quick-Band-Importance-Function (qBIF), is used during testing to approximate the inter- and intra-subject variability in these SII parameters.

In one form, the second step is an optimization process which operates on the results from the speech test and derives the desirable amount of gains for each frequency region. In another form, the optimization algorithm optimizes at least a portion of the speech test itself. The resulting gains for the individual may then be programmatically applied to the individual's prescribed hearing aid device(s).

Shown in FIG. 1 is one set of steps suitable for use in testing the hearing of an individual being fit for hearing aids using the above qBIF method. The process of FIG. 1 may occur in conjunction with or subsequent to audiometric testing (i.e. the measurement of the audiogram). The process begins at start point 100, and in step 102, the individual is prepared for the test by being seated or otherwise comfortably placed within a predefined testing environment. In one form, the testing equipment included within the testing environment includes one or more speakers, headphones or the like in order to present sound to the user. The testing environment may be located within a soundproof or a controlled low-ambient noise environment. In a further form, the speaker is placed in front of the individual, and preferably approximately 1 meter away. However, as is recognized in the art, alternate positions and environments may be utilized without departing from the scope of the present invention. Also provided may be a user input device, test monitor or other input mechanism whereby the user's performance in the test is provided as feedback.

The process proceeds to step 104 where the individual is instructed as to the procedures of the test. In one form, the user may be instructed to enter a response orally, physically or by using a touchscreen, a keyboard, a clicker device or some other user input device. In step 104, the individual may be instructed to recognize certain of the words spoken in the test sentences (i.e. the keywords) as much as possible. For example, in one form a list of words are presented to the individual on a touchscreen and as the individual hears one of the words on the screen the user is instructed to touch that word on the screen. In an alternate form, the user may be instructed to look for words that rhyme with a given word, words that start with a certain letter, or some other class of words that would be easily understood. In other forms, physical buttons may be utilized or the individual may be instructed to speak the words they hear back. In yet another form, the listener's task is to repeat the whole sentence verbally on every trial. The point is for the user to know which words or type of words to be on alert for, and to provide or effect some user input to confirm that they heard one of those words.

In step 106, the individual may be fitted with hearing aids as indicated by the traditional hearing aid fitting to provided amplification during testing, and the illustrated method will subsequently operate to improve this baseline. The process continues at step 108 with a series of multi-talker babble noise being presented to the individual through the speaker along with a target sentence or series of one or more words including one or more keywords. In the illustrated embodiment, the speech recognition of the individual in the multi-talker babble noise is measured through input based upon the user's performance (described below). This user's hearing may be aided or unaided. In one form, the speech signals to be played through the speaker are sentences, with each sentence consisting of multiple scoring keywords. On representative set of sentences for use is the IEEE sentences recorded by Galvin and Fu, 2003. In other forms, the speech signals may be one or more words, which either do or do not form a sentence.

In step 110, and according to the illustrated embodiment, the individual being tested provides input to the touchscreen or other input device, or otherwise alerts that they heard a keyword, in response to the sounds presented. In other forms, the input may be provided or collected on behalf of the user based on his/her responses and performance. In step 112, the results of steps 108 and 110 and processed according to a process described below with respect to FIG. 2. Returning to FIG. 1, steps 108 and 110 repeat a number of times with the stimuli presented to the user dynamically selected prior to each iteration. Following each iteration, the process determines whether or not additional iterations of steps 108 and 110 are required. This may be determined in many ways, such as determining the posterior standard deviation of BIF parameters and terminating the cycle when the posterior standard deviations at the 500-, 1000-, and 2000-Hz fall below a certain tolerance for a consecutive number of test trials, such as 2, 3, 4, 5 or the like. This tolerance can be set by the audiologist or the process administrator, with a high tolerance leading to a smaller number of test trials, and a low tolerance leading to a larger number of trials. Following the desired number of iterations initiated in step 112, the individual testing process arrives at an individualized and estimated SII model fit to the user, which can be used to generate predictions of speech intelligibility for any given hearing-aid prescriptions (step 114). The process subsequently concludes at step 116.

Steps 108 and 110, which occur as part of the process illustrated in FIG. 1, effect an iterative presentation of varied stimuli to the user. In the illustrated embodiment, these stimuli are not randomly selected, but rather are based upon the user's hearing characteristics determined thus far. Upon receipt of new results from the user during step 110, updated SII parameters ($w_i$, SRT, and $\beta$) are estimated via logistic regression based on the stimuli and responses from all previously completed trials. The interim estimate of the SII model is then used to determine which bands to present the target and masker in for the next trial and the TMR within these bands. This stimulus selection process optimizes the expected information gain by minimizing the entropy of the posterior parameter distribution.

Figure 2:
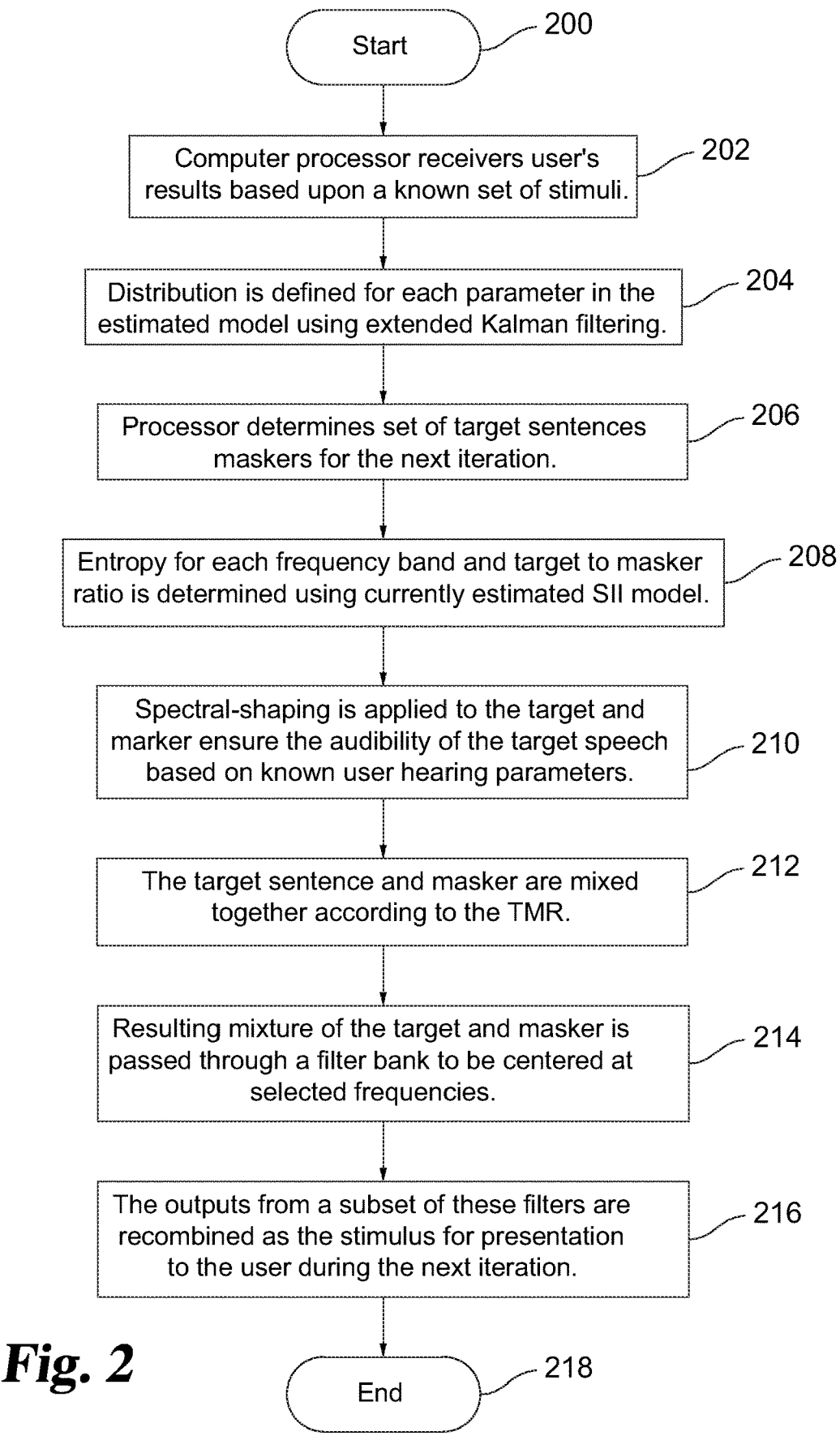
FIG. 2 is a flowchart illustrating further details for a process which takes place as part of the iterative portion of the process of FIG. 1.

Illustrated in FIG. 2, is a process 200 for accepting as input a user's response to known stimuli, determining and adjusting the estimated SII model for the user, and intelligently selecting the next set of stimuli for presentation to the user. Upon completion of the iterative process, the resulting estimated SII model is finalized as being fit for the user. The process begins at start point 200, and proceeds to receive the user's results obtained in response to a set of stimuli in step 202. Business logic analyzes the result using a processor. Specifically, after each iteration of steps 108 and 110, a distribution is defined for the parameters of the Speech Intelligibility Index (SII) model based, in part, upon the data collected (step 204). The parameter distribution is assumed to be multivariate Gaussian and can be described by a vector of means and covariance matrix. Following each trial, the parameter estimates of the Speech Intelligibility Index model are updated using methods such as the extended Kalman filtering method. This leads to a posterior parameter distribution, whose mean corresponds to an interim model fit. In other forms, a logistic regression or other method may be utilized.

Using the results, along with any prior available results for the user, a computer processor determines a set of possible stimuli for presentation to the user in the next iteration. To accomplish this, a target sentence and a masker are determined in step 206. For all possible frequency filtering bands and target to masker ratios (TMR) for the next trial, the expected entropy of the posterior distribution is calculated (stage 208). The best frequency filtering bands and target to masker ration that leads to the lowest expected entropy is selected for application to the stimulus prior to presentation as part of the next trial. In this manner, stimuli which are determined to be less helpful in arriving at an optimal solution are ignored in favor of those likely to provide the most value. Using this method, the qBIF procedure does not require the presentation of speech always in adjacent bands, optimal test results can be achieved using 200 to 300 words or less than 50 to 100 sentences, which is a significant improvement in time efficiency compared to previous low- and high-pass filtering methods.

Once selected, the target and masker may also be spectrally-shaped to ensure the audibility of the target speech for hearing-impaired listeners in step 210. For example, the target level may be fixed at 65 dB SPL before spectral shaping. This may occur based upon the traditional hearing aid fitting in the event that the method is performed upon an unaided user. The gains are applied to the target and masker in ⅓-octave bands according to the NAL-RP prescription formula. In case that the speech level in any of the ⅓-octave bands below 4000 Hz is less than 15 dB above the audiometric threshold after spectral shaping, additional gain is provided in those bands.

Next, in step 212, the target and masker are mixed together according to the TMR selected for the trial in step 208. The masker is gated on 0.5 s before the onset of the target sentence and gated off 0.5 s after the offset of the target sentence. Subsequently, in step 214, the mixture of the target and masker is passed through a filter bank with five one-octave-wide filters centered at 250, 500, 1000, 2000, and 4000 Hz. Each of the filters is constructed as a 12th order butterworth filter with 36 dB/oct roll-off at each of its cutoff frequencies. In step 216, the outputs from a subset of these filters are re-combined as the stimulus for the current trial. The subset of the filters to present the stimulus (i.e. Presentation Bands) were determined in step 208. It shall be appreciated that steps 210 and 212 may be omitted in the case of assisted hearing or have the order in which they occur with respect to the remaining steps altered depending upon the user. The process ends at end point 218.

In summary, during each qBIF run outlined in FIG. 2, an interim model is updated iteratively following each trial by fitting the individual's speech recognition performance model equation about to all completed trials of the same qBIF run. The stimulus presented on the following trial is then optimized using a one-step-ahead search algorithm, which selects the stimulus with the maximum expected information gain from all possible stimulus options considered. For the TMR, the potential values range from −5 to 15 dB in 5-dB steps. For the Presentation Bands, the number of bands to present the target speech and masker ranges from 2 to 4, which led to a total of 25 unique combinations of frequency bands.

At the beginning of a qBIF run, before the number of completed trials is sufficiently large to allow stable logistic fit, the one-step-ahead search algorithm of steps 206 and 208 of FIG. 2 is not activated. In the current implementation, a non-parametric adaptive tracking procedure is used to adjust the stimuli during the initial trials. The speech and masker are presented in five of the six bands, randomly drawn from trial to trial. The TMR is initially 15 dB. It was reduced by 10 dB following two consecutive trials in which more than half of the keywords are recognized correctly, and it is increased by 5 dB whenever the listener fails to recognize 50% or more keywords on a given trial. This adaptive tracking procedure terminates when the total number of reversals reaches 16 (typically ~35 trials), which activates the one-step-ahead search algorithm for stimulus sampling on subsequent trials. This adaptive procedure is able to adapt to individual listeners' performance levels, so that the expected performance during the initial trials would be close to 71%.

Figure 3:
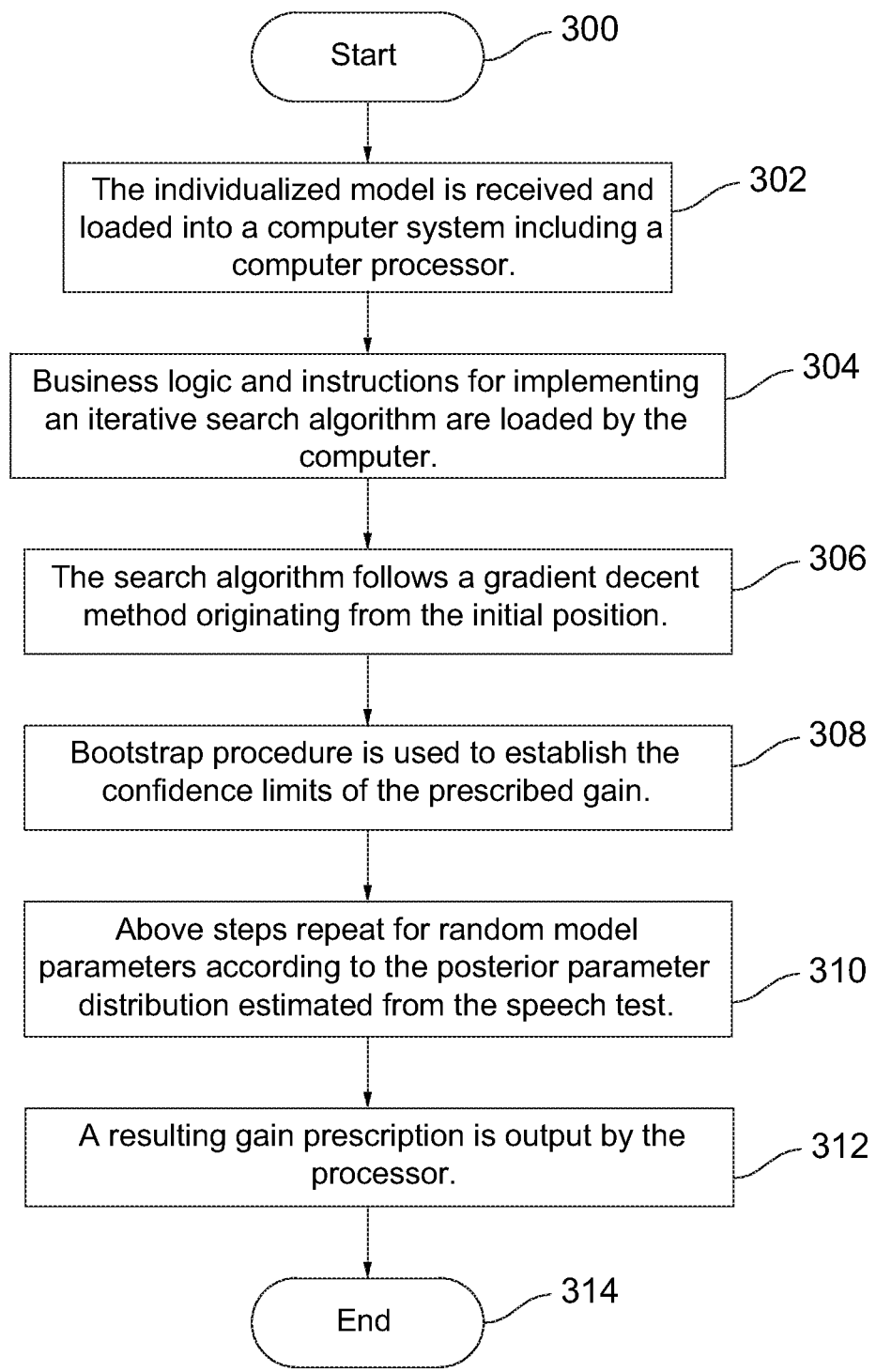
FIG. 3 is a flowchart illustrating an exemplary process for determining the optimal gain prescription for an individual.

Illustrated in FIG. 3 is one set of steps which may be performed in the process of determining the optimal gain prescription for an individual given an SII model. In the illustrated embodiment, the individualized estimated SII model achieved using the above method is utilized. However, it shall be appreciated that alternate hearing models may be utilized without departing from the scope of the present disclosure.

The process beings at start point 300 and in step 302 the individualized SII model is received and loaded into a computer system including one or more computer processors. The processor utilized may be the same as that utilized in performing the processes of FIG. 1 and/or FIG. 2 or may be a separate processor or set of processors. In step 304, business logic and instructions for implementing an iterative search algorithm that maximizes the speech intelligibility in a multi-dimensional gain space that represents the gain in each frequency band along each of its dimensions are loaded by the computer. One of skill in the art shall appreciate the algorithm for performing such a search, however, for purposes of example, the following pseudocode algorithm may be utilized:

```
bool IS (src, target, max_depth)
    for limit from 0 to max_depth
        if DLS(src, target, limit) == true
            return true
    return false
bool DLS(src, target, limit)
    if (src == target)
        return true;
    // If reached the maximum depth,
    // stop recursing.
    if (limit <= 0)
        return false;
    foreach adjacent i of src
        if DLS(i, target, limit?1)
            return true
    return false.
```

In step 306, in the illustrated embodiment, the search algorithm follows a gradient decent method originating from the initial position. It shall be appreciated that other methods of depth or breadth-wise decent may be utilized depending upon a variety of factors and the desired efficiency vs. accuracy. In step 308, a bootstrap procedure is used to establish the confidence limits of the prescribed gain. Bootstrapping is a statistical procedure that resamples a single dataset to create many simulated samples. This process allows the estimation of standard errors, construct confidence intervals, and perform hypothesis testing for numerous types of sample statistics, as will be appreciated by one of skill in the art. In step 310, this procedure repeats the above described search algorithm, for random model parameters according to the posterior parameter distribution estimated from the speech test. Upon conclusion of the algorithm, which may be specified by the user or the algorithm's completion, a resulting gain prescription is output by the processor is step 312. The process ends at step 316.

In one form, programming the programmable hearing aids is quick and efficient for the individual user of the hearing aid after receiving the hearing aid from a mail order service, purchasing it in the store over the courter or via a kiosk. Alternatively, a hearing aid dispenser can stock the programmable hearing aid in his/her office. Prior to about the time of purchasing the hearing aid, the above processes occurs, and the resulting gain prescription (from step 114) is entered into the computer and the hearing aid programmed immediately. The hearing aid may then be tried on the individual during this fitting process and readjusted, i.e., reprogrammed, immediately during this visit. The result is a system and method of programming hearing aids, and an actual programmed hearing aid, which minimizes the customer's waiting time and delivers an accurately programmed hearing aid which provides an enhanced effect for the individual. This also results in fewer returns of hearing aids from the dispenser to the manufacturer due to incorrect selection, adjustment or programming.

In another form, the hearing aid dispenser (the hearing health professional responsible for fitting the hearing aid to the individual) or the processor itself (via programmatic instructions) may communicate the resulting gain prescription for the individual to the manufacturer of the hearing aid along with an order for the hearing aid. The manufacturer may then select the appropriate hearing aid circuit with the appropriate frequency response. Alternatively, the manufacturer may take a stock hearing aid and adjust, or otherwise "program" the hearing aid, at the factory to compensate for the individual's specific hearing deficiency. The manufacturer, when the selection, adjustment or programming of the hearing aid is complete, may then send the hearing aid to the dispenser. The dispenser may then deliver the programmed hearing aid to the individual.

While the invention has been illustrated and described in detail in the drawings and foregoing description, the same is to be considered as illustrative and not restrictive in character, it being understood that only the preferred embodiment has been shown and described and that all equivalents, changes, and modifications that come within the spirit of the inventions as described herein and/or by the following claims are desired to be protected. Hence, the proper scope of the present invention should be determined only by the broadest interpretation of the claims so as to encompass all such modifications as well as all relationships equivalent to those illustrated in the drawings and described in the specification.

What is claimed is:

1. A method for fitting a programmable hearing aid to an individual in order to maximize speech intelligibility comprising the steps of:

providing to the individual through at least one speaker a set of audible stimuli, each comprising a target combined with a plurality of background noise, wherein the target comprises at least one keyword and the audible stimuli is filtered so as to include only a less than complete set of frequency bands;

determining the individual's perceived responses to each said stimulus within said set of audible stimuli by receiving user input based on the individual's hearing of the set of audible stimuli;

determining using a set of at least one computer processor a set of parameters for use within the Speech Intelligibility Index using said perceived responses;

iteratively refining the set of parameters using the set of at least one computer processor by generating a revised set of audible stimuli for providing to the user, wherein the frequency at which the revised audible stimuli is filtered is programmatically selected, and determining the individual's perceived responses to the revised audible stimuli by receiving user input based on the individual's hearing of the revised set of audible stimuli;

calculating, using the set of computer processors, a plurality of gain compensation factors for a plurality of frequencies at which the hearing aid operates using the set of parameters; and programmatically adjusting, using the computer processors, at least a first factor within said plurality of gain compensation factors using an iterative search algorithm to achieve increased speech intelligibility across at least a portion of the entire frequency spectrum; and programmatically setting, using the computer processors, at least a portion of the plurality of gain compensation factors into the programmable hearing aid as gain settings, including said first factor.

2. The method of claim 1, wherein the background noise is multi-talker babble noise.

3. The method of claim 2, wherein the target is contained within a spoken sentence.

4. The method of claim 1, wherein the target is contained within a spoken sentence.

5. The method for claim 1, wherein the target is comprised of at least two keywords.

6. The method of claim 5 wherein the target is spoken in one voice.

7. The method of claim 1, wherein the target is comprised of at least three keywords.

8. The method of claim 1, wherein the audible stimuli is filtered using at least one one-octave-wide filter which is centered at either 250, 500, 1000, 2000, or 4000 Hz.

9. The method of claim 1, wherein the set of parameters is determined using extended Kalman filtering.

10. The method of claim 1, wherein the set of parameters is determined using extended logistic regression.

11. The method of claim 1, wherein the plurality of gain compensation factors are determined using an iterative search algorithm.

12. The method of claim 1, wherein the user is wearing a hearing aid.

13. The method of claim 1, wherein the set of parameters are utilized in place of constants which are part of the Speech Intelligibility Index.

14. The method of claim 1, further comprising the step of mixing the target and the plurality of background noise at predetermined ratios.

15. A method for fitting a programmable hearing aid to an individual in order to maximize speech intelligibility comprising the steps of:

providing to the individual through at least one speaker a set of audible stimuli, each comprising a target combined with a plurality of background noise, wherein the target comprises at least one keyword and the audible stimuli is filtered so as to include only a less than complete set of frequency bands;

determining the individual's perceived responses to each said stimulus within said set of audible stimuli by receiving user input based on the individual's hearing of the set of audible stimuli;

determining using a set of at least one computer processor a set of parameters for use within the Speech Intelligibility Index using said perceived responses;

iteratively refining the set of parameters using the set of at least one computer processor by generating a revised set of audible stimuli for providing to the user, wherein the frequency at which the revised audible stimuli is filtered is programmatically selected, and determining the individual's perceived responses to the revised audible stimuli by receiving user input based on the individual's hearing of the revised set of audible stimuli;

calculating, using the a set of at least one computer processor, a plurality of gain compensation factors for a plurality of frequencies at which the hearing aid operates using the set of parameters; and programmatically adjusting, using the set of at least one computer processor, at least a first factor within said plurality of gain compensation factors using an iterative search algorithm to achieve increased speech intelligibility across at least a portion of the entire frequency spectrum; and setting at least a portion of the plurality of gain compensation factors into the programmable hearing aid as gain settings, including said first factor.

16. A method for fitting a programmable hearing aid to an individual in order to maximize speech intelligibility comprising the steps of:

providing to the individual through at least one speaker a set of audible stimuli, each comprising a target combined with a plurality of background noise, wherein the target comprises at least one keyword presented within a sentence and the audible stimuli is filtered so as to include only a less than complete set of frequency bands and mixed to achieve a predetermined volume ratio between the target and the plurality of background noise;

determining the individual's perceived responses to each said stimulus within said set of audible stimuli by receiving user input based on the individual's hearing of the set of audible stimuli;

determining using a set of at least one computer processor a set of parameters for use within the Speech Intelligibility Index using said perceived responses;

iteratively refining the set of parameters using the set of at least one computer processor by generating a revised set of audible stimuli for providing to the user, wherein the frequency at which the revised audible stimuli is filtered and the volume ratio at which target and the plurality of background noise are mixed is programmatically selected, and determining the individual's perceived responses to the revised audible stimuli by receiving user input based on the individual's hearing of the revised set of audible stimuli;

calculating, using the set of at least one computer processor, a plurality of gain compensation factors for a plurality of frequencies at which the hearing aid operates using the set of parameters; and programmatically adjusting, using the set of at least one computer processor, at least a first factor within said plurality of gain compensation factors using an iterative search algorithm to achieve increased speech intelligibility across at least a portion of the entire frequency spectrum; and setting at least a portion of the plurality of gain compensation factors into the programmable hearing aid as gain settings, including said first factor.

\* \* \* \* \*

UNITED STATES PATENT AND TRADEMARK OFFICE
CERTIFICATE OF CORRECTION

PATENT NO. : 11,611,838 B2
APPLICATION NO. : 17/309945
DATED : March 21, 2023
INVENTOR(S) : Yi Shen It is certified that error appears in the above-identified patent and that said Letters Patent is hereby corrected as shown below:

On the Title Page

Item (54), replace "SYSTEM AND METHOD FOR INDIVIDUALIZED HEARING AIR PRESCRIPTION" with --SYSTEM AND METHOD FOR INDIVIDUALIZED HEARING AID PRESCRIPTION--

In the Specification

Column 1, Lines 1-3, replace "SYSTEM AND METHOD FOR INDIVIDUALIZED HEARING AIR PRESCRIPTION" with --SYSTEM AND METHOD FOR INDIVIDUALIZED HEARING AID PRESCRIPTION--

Signed and Sealed this
Thirtieth Day of May, 2023

*Katherine Kelly Vidal*

Katherine Kelly Vidal
*Director of the United States Patent and Trademark Office*